US011166744B2

United States Patent
Morrissette et al.

(10) Patent No.: US 11,166,744 B2
(45) Date of Patent: Nov. 9, 2021

(54) ELECTRICALLY CONDUCTIVE REDUCER DEVICE, RELATED SYSTEMS, AND RELATED METHODS

(71) Applicant: Intuitive Surgical Operations, Inc., Sunnyvale, CA (US)

(72) Inventors: Tyler Morrissette, Niantic, CT (US); Justin Krom, Southington, CT (US); Joseph Orban, III, Norwalk, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 798 days.

(21) Appl. No.: 15/809,372

(22) Filed: Nov. 10, 2017

(65) Prior Publication Data
US 2018/0132890 A1 May 17, 2018

Related U.S. Application Data

(60) Provisional application No. 62/421,717, filed on Nov. 14, 2016.

(51) Int. Cl.
*A61B 17/34* (2006.01)
*A61B 18/00* (2006.01)
(Continued)

(52) U.S. Cl.
CPC ...... *A61B 17/3423* (2013.01); *A61B 17/3421* (2013.01); *A61B 18/00* (2013.01);
(Continued)

(58) Field of Classification Search
CPC ............ A61B 17/3421; A61B 31/3423; A61B 2018/00071; A61B 17/3462;
(Continued)

(56) References Cited

U.S. PATENT DOCUMENTS 5,387,196 A * 2/1995 Green ............... A61B 17/34
128/908
6,193,717 B1 * 2/2001 Ouchi ............... A61B 18/1477
604/114

(Continued)

FOREIGN PATENT DOCUMENTS

WO WO-2015142794 A1 9/2015

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Anu Ramana
(74) *Attorney, Agent, or Firm* — Jones Robb, PLLC

(57) ABSTRACT

A reducer device for insertion into a surgical cannula includes a tubular member having a proximal opening and a distal opening and an electrically conductive component configured and positioned to provide an electrically conductive path from an interior of the tubular member to an exterior of the tubular member. The electrically conductive path is localized along an axial length of the tubular member. A method of configuring a surgical device includes positioning a surgical cannula within an incision of a patient's body wall, positioning a reducer device within the surgical cannula, and positioning a surgical instrument within the reducer device. Positioning the surgical instrument within the reducer device includes forming an electrically conductive pathway between the surgical cannula and the surgical instrument.

19 Claims, 8 Drawing Sheets

(51) Int. Cl.
*A61B 17/00* (2006.01)
*A61M 13/00* (2006.01)

(52) U.S. Cl.
CPC ....... *A61B 17/3439* (2013.01); *A61B 17/3478* (2013.01); *A61B 2017/00929* (2013.01); *A61M 13/003* (2013.01)

(58) Field of Classification Search
CPC ........ A61B 17/3439; A61B 2017/3441; A61B 1/00131; A61B 1/00135; A61B 1/00137; A61B 1/00154; A61M 2039/0626; A61M 2039/0279
See application file for complete search history.

(56) References Cited

U.S. PATENT DOCUMENTS

| | | |
|---|---|---|
| 8,545,515 B2 | 10/2013 | Prisco et al. |
| 8,852,208 B2 | 10/2014 | Gomez et al. |
| 2007/0270752 A1* | 11/2007 | LaBombard ........... A61B 17/34 604/164.01 |
| 2010/0185053 A1* | 7/2010 | Hagen ................ A61B 17/3431 600/114 |
| 2013/0096555 A1* | 4/2013 | Krom .................... A61B 18/12 606/41 |
| 2013/0325031 A1 | 12/2013 | Schena et al. |
| 2013/0325033 A1 | 12/2013 | Schena et al. |

\* cited by examiner

ELECTRICALLY CONDUCTIVE REDUCER DEVICE, RELATED SYSTEMS, AND RELATED METHODS

RELATED APPLICATIONS

This patent application claims priority to and the benefit of the filing date of U.S. Provisional Patent Application 62/421,717, entitled "ELECTRICALLY CONDUCTIVE REDUCER DEVICE, RELATED SYSTEMS, AND RELATED METHODS" filed Nov. 14, 2016, which is incorporated by reference herein in its entirety.

TECHNICAL FIELD

Aspects of the present disclosure relate to reducer devices for surgical cannulas, and related systems and methods.

INTRODUCTION

To facilitate various surgical procedures, a trocar assembly is inserted in an incision through a patient's epidermis. The trocar assembly includes a surgical cannula, an obturator at a distal end of the cannula, and a seal at a proximal end of the cannula. A portion of the trocar assembly is inserted through the incision and pierces the body wall, enabling the cannula to reach a surgical location. Various surgical instruments or tools can be positioned to extend through the cannula to the surgical location to perform a surgical procedure. Such instruments include, for example and without limitation, tools configured to seal, bond, ablate, fulgurate, or perform other treatments of tissue through application of an electrical current. Other instruments include optical instruments, such as an endoscope, or instruments configured to suture, staple, apply clips to blood vessels, etc.

Different instruments sometimes require different sized of cannulas. For example, some instruments have an outside shaft diameter relatively larger than an outside shaft diameter of other instruments, and thus require a cannula with a correspondingly larger cannula inside diameter to accommodate the instrument. To impart efficiency to the surgical process and reduce (e.g., minimize) trauma to the patient that could result from removal of a cannula and insertion of a different (e.g., larger) cannula in the same incision when needed to accommodate a different instrument, the largest cannula that will be required during the procedure is inserted, and the effective inside diameter of the large cannula is reduced to the inside diameter required by a smaller instrument by a reducer device. The reducer device has an exterior diameter sized to fit within the large internal diameter cannula, and an interior diameter sized to accept and support the relatively smaller diameter instrument.

Some surgical tools that utilize electrical power are susceptible to capacitive coupling with other surgical tools, such as other instruments, cannulas, etc. during use. Capacitive coupling can generate a leakage current in the surgical tool which, if not dissipated in a controlled and predictable manner, could potentially result in misdirection of electrical energy. In some cases, the cannula is made from a conductive material, such as a metal or alloy, and contact or sufficient proximity between the conductive cannula and a conductive portion of the instrument permits a conductive pathway from the instrument to the cannula to dissipate any leakage current to the patient's body wall through the outer surface of the conductive cannula, with the patient typically being further electrically grounded via a return pad to a ground terminal. However, the reducer devices discussed above are typically made from materials such as polymers, etc. that are electrically insulative in order to reduce the cost of and facilitate manufacturing. Such reducer devices can thus interfere with the creation of the electrically conductive pathway between the instrument (inserted through the reducer device) and the cannula, which can pose issues for dissipating electrical energy from the instrument when the instrument is subject to capacitive coupling.

A need exists to provide a conductive path between a conductive cannula and an instrument that is inserted through a reducer device positioned within the cannula. It is desirable to provide such a conductive path while providing reducer devices that are relatively inexpensive to manufacture.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a reducer device for insertion into a surgical cannula includes a tubular member having a proximal opening and a distal opening and an electrically conductive component configured and positioned to provide an electrically conductive path from an interior of the tubular member to an exterior of the tubular member. The electrically conductive path is localized along an axial length of the tubular member.

In accordance with at least another exemplary embodiment, a surgical assembly includes a surgical cannula, a reducer device configured to be inserted within the surgical cannula, and a surgical instrument configured to be inserted within the reducer device. The reducer device includes an electrically conductive structure that forms an electrically conductive path between the surgical instrument and the surgical cannula.

In accordance with yet another exemplary embodiment, a method of configuring a surgical device includes positioning a surgical cannula within an incision of a patient's body wall, positioning a reducer device within the surgical cannula, and positioning a surgical instrument within the reducer device. Positioning the surgical instrument within the reducer device includes forming an electrically conductive pathway between the surgical cannula and the surgical instrument.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
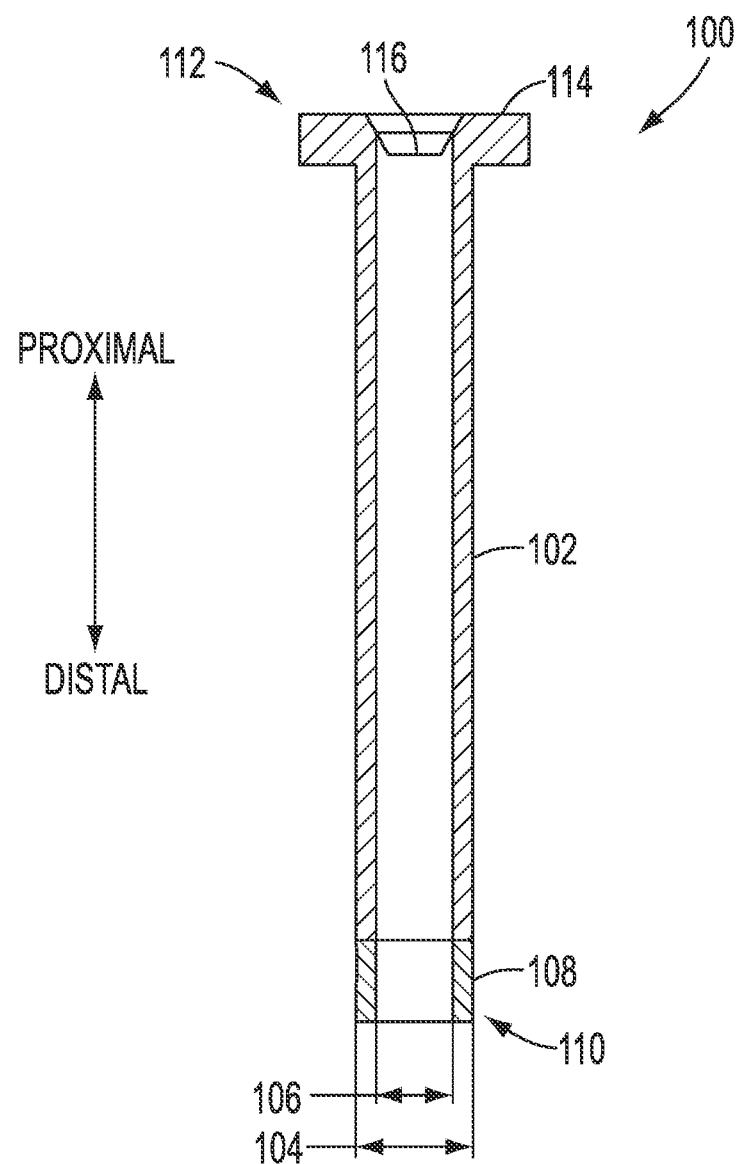
FIG. 1 is a cross-sectional elevation view of a reducer device according to an exemplary embodiment of the disclosure.

The present disclosure contemplates various exemplary embodiments of reducer devices configured to define an electrically conductive path exhibiting a lower electrical resistance than other portions of the reducer device. Features of a reducer device that provide the electrically conductive path can be sufficiently electrically conductive relative to other portions of the reducer devices such that current, such as leakage current from a surgical instrument inserted through the reducer device, tends to flow through the electrically conductive path to another electrically conductive structure in the vicinity of the reducer device, such as a conductive cannula within which the reducer device is positioned. Various exemplary embodiments of reducer devices according to the present disclosure additionally contemplate using various elements and structural configurations of reducer devices that promote reliable positioning of the reducer device within a cannula so as to achieve contact or sufficiently close proximity between the features of the reducer device creating the electrically conductive pathway and the inner wall of the cannula.

In one exemplary embodiment, the reducer device includes a tubular portion with a main tube portion and an electrically conductive tube portion. For example, the main tube portion is made of an electrically insulative material and the electrically conductive component is coupled with the main tube portion. The electrically conductive component is configured to form a conductive path between a shaft of a surgical instrument inserted through the main tube portion of the reducer device and the conductive cannula. In some exemplary embodiments, the conductive path is localized along an axial length of the reducer device. As used herein, "electrically conductive" materials refer to those that exhibit lower electrical resistance as compared to other materials typically recognized as insulators, such as polymers, ceramics, glass, etc. Such electrically conductive materials can include, but are not limited to, metals, metal alloys, conductive polymers, graphite, or other materials.

In an exemplary embodiment, the reducer device comprises a protrusion extending radially outwardly from an outer surface of the main tube portion. The protrusion is sized and configured to abut against a component in the vicinity of the reducer device. For example, the protrusion is sized and configured to abut against an inside wall of the cannula in an inserted position of the reducer device within the cannula. The interaction of the protrusion and the inside wall of the cannula biases the main tube portion away from a coaxial relationship with the cannula in a manner that positions the electrically conductive portion against or in close proximity to the inside wall of the conductive cannula. In this way, a consistent and reliable contact between the electrically conductive portion and the conductive cannula is achieved.

In other exemplary embodiments, the electrically conductive component of the reducer device is elastically deformable. In one exemplary embodiment, the elastically deformable conductive component includes at least one flexible arm configured with portions that extend beyond an outer surface or beyond an inner surface of a main tube of the reducer device in an unbiased position. In an exemplary embodiment, the at least one flexible arm includes a free end configured to extend beyond the outer surface of the main tube, and an elbow portion configured to extend beyond the inner surface of the main tube. In an exemplary embodiment, the free end is biased into contact with a conductive instrument, such as a shaft of a surgical instrument, when the shaft of the surgical instrument is inserted within the reducer device. The elbow portion is also biased into contact with another conductive structure in the vicinity of the reducer device, such as a conductive cannula. In the biased position, the free end is preloaded against the shaft of the surgical instrument, and the elbow portion is preloaded against the conductive cannula.

In some exemplary embodiments, the elastically deformable conductive component further includes a coil configured to circumferentially surround the main tube portion of the reducer device and couple the flexible arm with the main tube portion of the reducer device. In some embodiments, the elastically deformable conductive component includes multiple flexible arms arranged to provide redundant points of contact inside and outside the main tube of the reducer device.

Exemplary embodiments described herein can be used, for example, with teleoperated, computer-assisted surgical systems (sometimes referred to as robotic surgical systems) such as those described in, for example, U.S. Patent App. Pub. No. US 2013/0325033 A1 (published Dec. 5, 2013), entitled "Multi-Port Surgical Robotic System Architecture," U.S. Patent App. Pub. No. US 2013/0325031 A1 (published Dec. 5, 2013), entitled "Redundant Axis and Degree of Freedom for Hardware-Constrained Remote Center Robotic Manipulator," and U.S. Pat. No. 8,852,208 (issued Oct. 7, 2014), entitled "Surgical System Instrument Mounting," and U.S. Pat. No. 8,545,515 (issued Oct. 1, 2013), entitled Curved Cannula Surgical System, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. Although various exemplary embodiments described herein are discussed with regard to surgical instruments used with a patient side cart of a teleoperated surgical system, the present disclosure is not limited to use with surgical instruments for a teleoperated surgical system. For example, various exemplary embodiments of reducer devices described herein can optionally be used in conjunction with hand-held, manual surgical instruments, such as laparoscopic instruments.

Referring now to FIG. 1, an exemplary embodiment of a reducer device 100 according to the disclosure is shown schematically. The reducer device 100 includes a main tube portion 102 with an outside diameter (OD) 104 and an inside diameter (ID) 106. The main tube portion 102 of the reducer device 100 has a proximal end 112, from which, in the exemplary embodiment of FIG. 1, a latch mechanism 114 (shown schematically in FIG. 1) extends and is configured to couple the reducer device with a cannula (such as cannula 218 shown in FIG. 2 discussed below). A seal 116 is located within the ID 106 of the main tube portion 102 of the reducer device 100. The seal 116 is configured to prevent loss of insufflation at the surgical site while a surgical instrument shaft (such as surgical instrument shaft 419 shown in FIG. 5 discussed below) is inserted through the seal 116 and through the cannula on to the surgical site to perform a surgical procedure. In addition, in the exemplary embodiment of FIG. 1, the seal 116 maintains a sterile environment distally past the seal 116. Additional details regarding the general configuration and use of the reducer device 100, including details regarding the latch mechanism 114 and seal 116, are disclosed in Intl Pub. No. WO2015/142794 A1 (published Sep. 24, 2015) titled CANNULA SEAL ASSEMBLY, the entire disclosure of which is incorporated by reference herein.

The reducer device 100 also includes an electrically conductive component 108. As shown in FIG. 1, the electrically conductive component 108 (e.g., an electrically conductive tube portion) is a short tube portion that extends distally from the distal end 110 of the main tube portion 102. The main tube portion 102 and the electrically conductive tube portion 108 together form a tubular member 101 of the reducer device 100. While the electrically conductive tube portion 108 extends distally from the main tube portion 102 in the exemplary embodiment of FIG. 1, the disclosure is not so limited and the electrically conductive component 108 can be a short tube portion positioned at other locations along the length of the reducer device 100, thus potentially dividing the main tube portion into axially separated sections along the length of the tubular portion of the reducer device.

In the exemplary embodiment of FIG. 1, the main tube portion 102 is made from a polymer, a composite material, or other generally electrically insulative material. As a non-limiting example, the main tube portion 102 is made from a polymer material such as polycarbonate, polypropylene, polyethylene, acrylonitrile butadiene styrene (ABS), or other polymers. Such materials exhibit various desirable characteristics for use as the main tube portion 102 of the reducer device 100. For example, polymer materials such as those identified above are generally low-cost in terms of raw materials, are relatively easily formed, such as by injection molding, and exhibit mechanical characteristics such as tensile and compressive strength sufficient to provide support to a surgical instrument shaft configured to be positioned within the ID 106 of the main tube portion 102, as discussed further below.

Such polymer materials generally exhibit a high level of electrical resistivity (i.e., low levels of electrical conductivity). The electrically conductive component 108 forms a conductive path from an interior surface of the reducer device to an exterior surface of the reducer device. For example, the electrically conductive component is configured to form a conductive path between a surgical instrument shaft positioned within the reducer device and a conductive cannula surrounding the reducer device in order to facilitate dissipation of an electrical current from the surgical instrument shaft to the conductive cannula.

Figure 2:
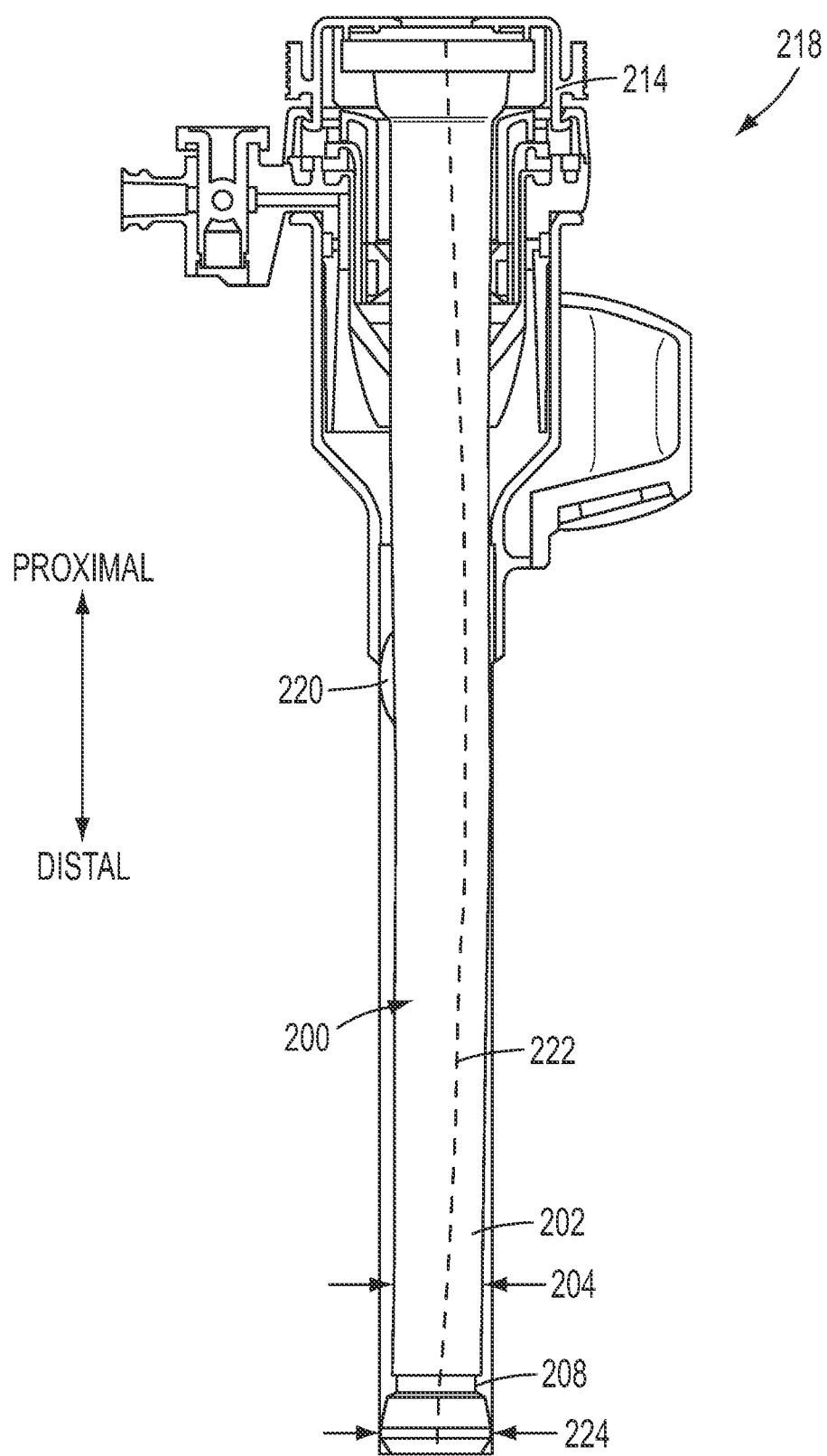
FIG. 2 is a partial cross-sectional elevation view of a reducer device, cannula, and seal according to another exemplary embodiment of the disclosure.

Referring now to FIG. 2, another exemplary embodiment of a reducer device 200 is shown positioned within a surgical cannula 218. In the exemplary embodiment of FIG. 2, the surgical cannula 218 is made from an electrically conductive material, such as a metal or metal alloy. As a non-limiting example, at least a portion of the surgical cannula 218 is made from stainless steel, such as an 18-8 chromium-nickel austenitic stainless steel, or other stainless steel alloys, such as 17-4 chromium-nickel martensitic stainless steel, SAE grade 316L stainless steel, 465 stainless steel, etc. Optionally, the surgical cannula 218 is made from other metals or metal alloys, such as titanium or titanium alloys, aluminum alloys, etc. In some exemplary embodiments, the material of the surgical cannula 218 is chosen in part based on the electrical conductivity of the material. In addition, the material of the surgical cannula 218 is optionally chosen based at least in part on the ability of the material to withstand a sterilization procedure, such as, for example, autoclave sterilization.

A latch mechanism 214 of the reducer device 200 is configured to couple the reducer device 200 with the cannula 218 to maintain the reducer device in position within the cannula. In the exemplary embodiment of FIG. 2, the reducer device 200 includes an electrically conductive component that is an electrically conductive short tube portion 208 positioned at a distal end 210 of a main tube portion 202 of the reducer device 200. As a non-limiting example, the electrically conductive tube portion 208 is made from materials similar to those noted above in connection with the cannula 218, such as stainless steel or other metals or metal alloys.

In the embodiment of FIG. 2, the electrically conductive tube portion 208 and the main tube portion 202 each include various features configured to ensure contact or close proximity between the electrically conductive tube portion 208 with an interior wall of the cannula 218 in the inserted and coupled position of the reducer device 200 and cannula 218. For example, as described in greater detail below in connection with FIG. 3, the electrically conductive tube portion 208 exhibits a maximum outer diameter 224 greater than an outer diameter 204 of the main tube portion 202 of the reducer device 200. Stated another way, in some exemplary embodiments, a clearance between the electrically conductive tube portion 208 and the interior wall of the cannula 218 is less than a clearance between the outer diameter 204 of the main tube 202 and the interior wall of the cannula 218. As a non-limiting example, the clearance between the interior wall of the cannula 218 and the main tube 202 of the reducer device 200 ranges from 0.010 inches (0.254 millimeters) to 0.020 inches (0.508 millimeters). As a non-limiting example, the clearance between the interior wall of the cannula 218 and the electrically conductive component 208 ranges from 0.001 inches (0.254 millimeters) to 0.005 inches (0.127 millimeters). These values are provided for example only, and any clearance dimension, whether inside or outside of the above ranges, is considered within the scope of the present disclosure.

A tighter clearance between the electrically conductive tube portion 208 and the inside wall of the cannula 218 than between the main tube 202 of the reducer device 200 and the inside wall of the cannula 218 facilitates consistent contact or close proximity between the electrically conductive tube portion 208 and the cannula 218. In exemplary embodiments, additional features of the main tube portion 202 of the reducer device 200 further contribute to consistent and reliable contact or close proximity between the electrically conductive component 208 and the cannula 218.

For example, in the exemplary embodiment of FIG. 2, the main tube portion 202 of the reducer device 200 includes a protrusion 220 extending radially outward from a location on the outer diameter 204 of the main tube portion 202 of the reducer device 200. The protrusion 220 forces the main tube portion 202 away from a central position within the cannula 218 (i.e., a position in which the main tube portion 202 would be centrally positioned along the entire length of the cannula 218) to a position in which at least a portion of the length of the main tube portion 202 is radially offset relative to the longitudinal axis of the cannula 218, as shown in FIG. 2 and indicated by dashed line 222. Stated another way, the protrusion 220 offsets the longitudinal axis of the main tube portion 202 relative to the longitudinal axis of the cannula 218.

The offset of the main tube portion 202 biases (e.g., preloads) the electrically conductive tube portion 208 into close proximity, or actual contact, with the inside wall of the cannula 218. Contact or close proximity between the electrically conductive tube portion 208 and the inside wall of the cannula 218 ensures electrical conduction between the electrically conductive tube portion 208 and the cannula 218, thereby facilitating conduction of a leakage current from a surgical instrument inserted through the reducer device through the electrically conductive tube portion and the cannula 218 to the body wall. The preloaded positioning of the electrically conductive tube portion 208 against or sufficiently close to the inside wall of the cannula 218 ensures that the electrically conductive tube portion 208 remains in contact or close proximity with the inside wall of the cannula 218 even when subject to forces such as gravity, or forces applied by manipulation or other operations of the surgical instrument.

Figure 3:
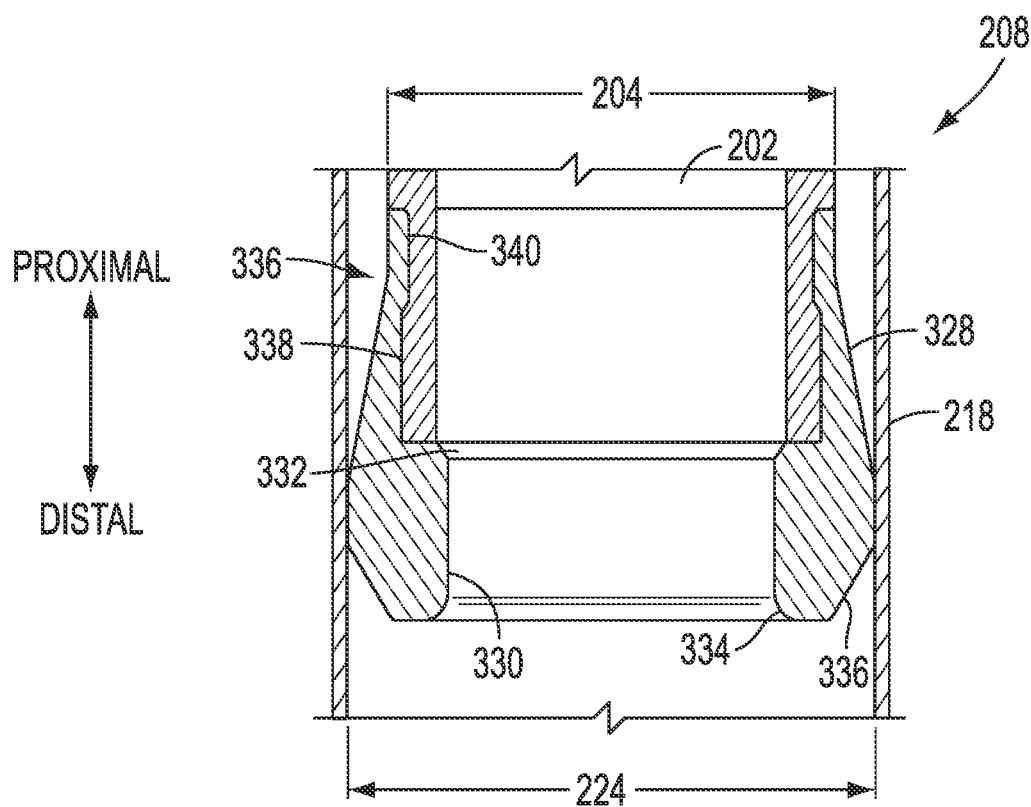
FIG. 3 is a cross-sectional enlarged view of a distal end of the reducer device according to the exemplary embodiment of FIG. 2.

FIG. 3 shows an enlarged view of the electrically conductive tube portion 208 of FIG. 2. As shown in FIG. 3, the electrically conductive tube portion 208 exhibits an outer diameter 224 greater than the outer diameter 204 of the main tube portion 202 of the reducer device 200 (FIG. 2). Thus, a clearance between the outer diameter 224 of the electrically conductive tube portion 208 and the interior wall of the cannula 218 is less than the clearance between the main tube portion 202 and the interior wall of the cannula 218.

In the exemplary embodiment of FIG. 3, the outer surface of the electrically conductive tube portion 208 has chamfers 326 and 328. The chamfers 326 and 328 facilitate insertion and withdrawal of the reducer device 200 through the seal 216 (FIG. 2) of the cannula 218 by providing a gradual (e.g., tapered) increase in diameter from the diameter 204 of the main tube portion 202 to the larger diameter 224 of the electrically conductive tube portion 208, thereby eliminating any shoulders (e.g., abrupt diameter changes) that could catch or hang up on other components as the reducer device 200 is inserted or withdrawn through the seal 216 and cannula 218.

Figure 4:
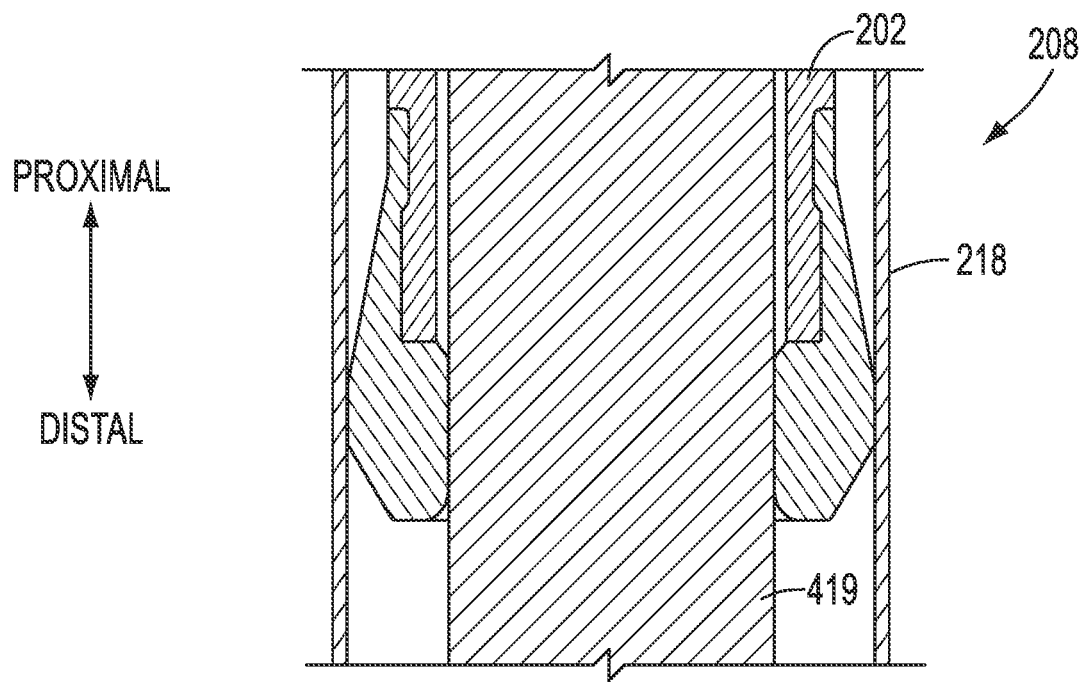
FIG. 4 is a cross-sectional enlarged view of the distal end of the reducer device of FIG. 2 with a surgical instrument shaft according to an exemplary embodiment of the disclosure.

An internal diameter 330 of the electrically conductive tube portion 208 is smaller than an internal diameter (e.g., internal diameter 106 indicated in FIG. 1) of the main tube portion 202 of the reducer device 200. In an exemplary embodiment, the internal diameter 330 is chosen for a close slip fit around the surgical instrument shaft 419 shown in FIG. 4. For example, the clearance between the internal diameter 330 of the electrically conductive tube portion 208 and the surgical instrument shaft 419 may range from 0.001 inches (0.0254 mm) to 0.005 inches (0.127 mm). However, the preceding range is non-limiting and clearances of less than 0.001 inches and greater than 0.005 inches are encompassed by the present disclosure. In an exemplary embodiment, the close fit between the surgical instrument shaft 419 and the internal diameter 330 of the electrically conductive tube portion 208 ensures consistent conductive contact or close proximity between the surgical instrument shaft 419 and the electrically conductive component 208. For example, the close fit between the surgical instrument shaft 419 and the internal diameter 330 of the electrically conductive tube portion 208 ensures that some portion of the surgical instrument shaft 419 is in conductive contact or proximity with the electrically conductive component 208 at all times during use of the instrument. For example, in the embodiment of FIGS. 2 through 4, even if the surgical instrument shaft 419 is not in actual, physical contact with the electrically conductive component 208, the gap between the surgical instrument shaft 419 and the electrically conductive component 208 is small enough that the resistance to electrical current flow between the surgical instrument shaft 419 and the electrically conductive tube portion 208 is similar to the resistance when the surgical instrument shaft 419 is in actual physical contact with the electrically conductive tube portion 208.

The electrically conductive tube portion 208 includes a chamfer 332 providing a gradual (e.g., tapered) transition between the interior diameter 330 and the interior diameter of the main tube portion 202. This can facilitate insertion of the surgical instrument shaft 419 within the interior diameter 330 of the electrically conductive tube portion 208 by guiding the surgical instrument shaft 419 into the interior diameter 330 of the electrically conductive tube portion 208 as the instrument shaft 419 is inserted from a proximal end of the reducer 200 (FIG. 2) toward a distal end of the reducer device 200. The chamfer 332 also facilitates passage of other items through the cannula and reducer device, such as needles, when the surgical instrument shaft 419 is not inserted within the reducer device 200. An edge radius 334 at the distal end of the electrically conductive tube portion 208 facilitates withdrawal of the surgical instrument shaft 419 from the electrically conductive tube portion 208, for example, by eliminating any abrupt shoulder on the electrically conductive tube portion 208 that could catch against asperities or other irregularities on the surgical instrument shaft 419 or a tip or jaw of the instrument.

Referring again to FIG. 3, the electrically conductive tube portion 208 also includes features configured to facilitate retention between the electrically conductive tube portion 208 and the main tube portion 202 of the reducer device 200 (FIG. 2). For example, the electrically conductive tube portion 208 includes a sleeve portion 336 with an undercut area 338. According to one exemplary embodiment, manufacture includes coupling the main tube portion 202 with the electrically conductive tube portion 208 using molding techniques. For example, in one exemplary molding technique, the electrically conductive tube portion 208 is placed in a mold for injection molding the main tube portion 202, and the main tube portion 202 is molded within the sleeve portion 336 and in the undercut area 338 of the electrically conductive tube portion 208. The material of the main tube portion 202 within the undercut area ensures the electrically conductive tube portion 208 remains affixed to the main tube portion 202. Configurations other than that shown in FIG. 3 are considered within the scope of the disclosure. For example, in another exemplary embodiment, the undercut area 338 is positioned on an outer surface of the sleeve portion 336, and the material of the main tube portion 202 is molded externally around the sleeve portion 336, rather than inside the sleeve portion 336 as shown in FIG. 3. Other features and methods for retaining the electrically conductive tube portion 208 and the main tube portion 202 together, such as adhesive bonding, heat staking, threads, interference fit between the main tube portion 202 and the electrically conductive tube portion 208, or other features and methods are considered within the scope of the present disclosure and would be understood by those having ordinary skill in the art in view of the present disclosure.

In the exemplary embodiment of FIG. 3, the undercut area 338 has an undercut depth that ranges, for example, from 0.003 inches (0.0762 millimeters) to 0.015 inches (0.381 millimeters) relative to a non-undercut portion 340 of the sleeve portion 336. As an additional, non-limiting example, the undercut area 338 is undercut relative to the non-undercut portion 340 by a nominal dimension of 0.01 inches (0.254 millimeters). Such dimensions and ranges are exemplary only, and the amount of undercut is chosen based on considerations such as, for example, to ensure retention of the electrically conductive tube portion 208 with the main tube portion 202 by providing a mechanical connection strong enough to withstand a tensile force applied to the electrically conductive component 208 of at least, for example, 1 pound force (lbf) (4.448 newtons (N)), or, for example, at least 5 lbf (22.24 N).

Figure 5:
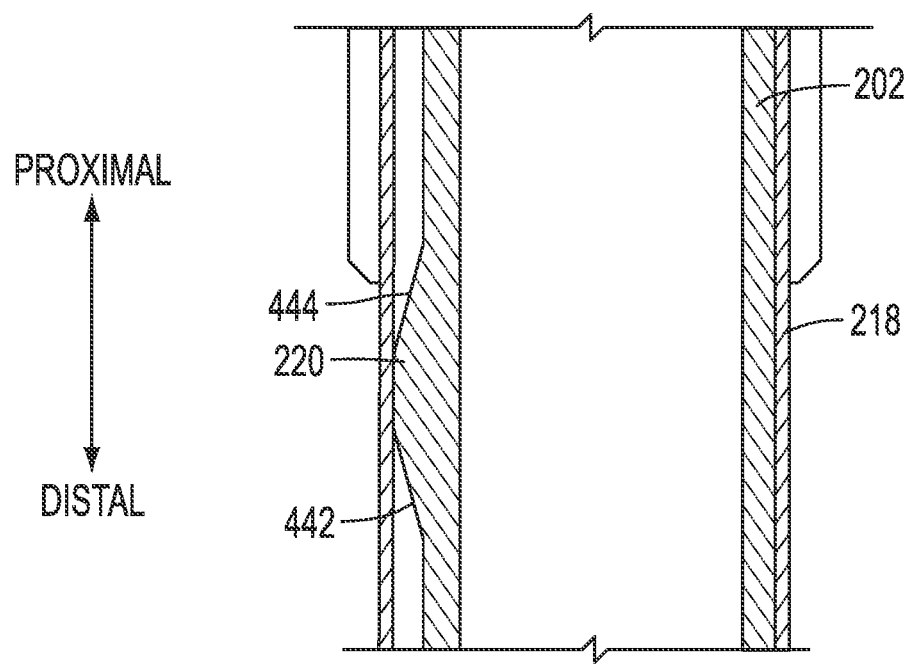
FIG. 5 is a partial cross-sectional enlarged view of a portion of the reducer device according to the exemplary embodiment of FIG. 2.

Referring now to FIG. 5, a detail view of the protrusion 220 extending from the main tube portion 202 as discussed in connection with FIG. 2 is shown. The distance the protrusion 220 extends from the outer surface of the main tube portion 202 is chosen based on the clearance between the main tube portion 202 and the cannula 218. As a non-limiting example, if the main tube portion 202 has a nominal outer diameter 204 of 0.01 inches (0.254 mm) less than a nominal inside diameter of the cannula 218, the height, h, of the protrusion 220 is chosen to be equal to or greater than 0.01 inches. As an additional, non-limiting example, the height h of the protrusion 220 is at least 0.05 inches (0.127 mm). The height h of the protrusion is chosen such that the main tube portion 202 is deflected from a coaxial position within the cannula 218 (FIG. 2) to bias the electrically conductive tube portion 208 against the cannula 218 to maintain conductive contact or proximity between the electrically conductive tube portion 208 and the cannula 218 under gravitational forces, forces associated with operation or manipulation of a surgical instrument, etc., as discussed above.

In an exemplary embodiment, the protrusion 220 includes ramp portions 442 and 444 configured to ensure smooth insertion and withdrawal of the reducer device 200 within the cannula 218 and seal 216 by preventing the protrusion 220 from interfering with (e.g., catching on, hanging up against) any portions of the cannula 218 and seal 216 as the reducer device 200 is inserted or withdrawn from the cannula 218. For example, in an exemplary embodiment, the ramp portions 442 and 444 are longitudinally oriented along a portion of the length of the reducer device 200. Stated another way, the direction of the slope of the ramp portions 442 and 444 is aligned with the central axis of the reducer device 200.

In some cases, in addition to a surgical cannula providing a passage for inserting a surgical instrument within a patient's body to obtain access to a surgical site, the cannula also provides a passage for insufflation of the surgical site (e.g., by applying a positive pressure gas to the cannula interior) or evacuation of smoke, gasses, or other material from the surgical site. As discussed above, in an exemplary embodiment, the clearance between the electrically conductive tube portion 208 and the cannula 218 is smaller than the clearance between the main tube portion 202 of the reducer device 200 and the cannula 218. While the clearance between the main tube portion 202 and the cannula 218 is sufficient to enable flow of insufflation or other gasses through the annulus between the main tube portion 202 and the cannula 218, the tighter clearance between the electrically conductive tube portion 208 and the cannula 218 can impede flow of such gasses. Accordingly, in exemplary embodiments, the reducer device 200 includes features configured to facilitate flow of gas and/or liquid through the cannula 218 and around the reducer device 200. For example, the electrically conductive component includes one or more features that form passages through which gas and/or liquid can flow when the reducer device is positioned within the cannula.

Figure 6:
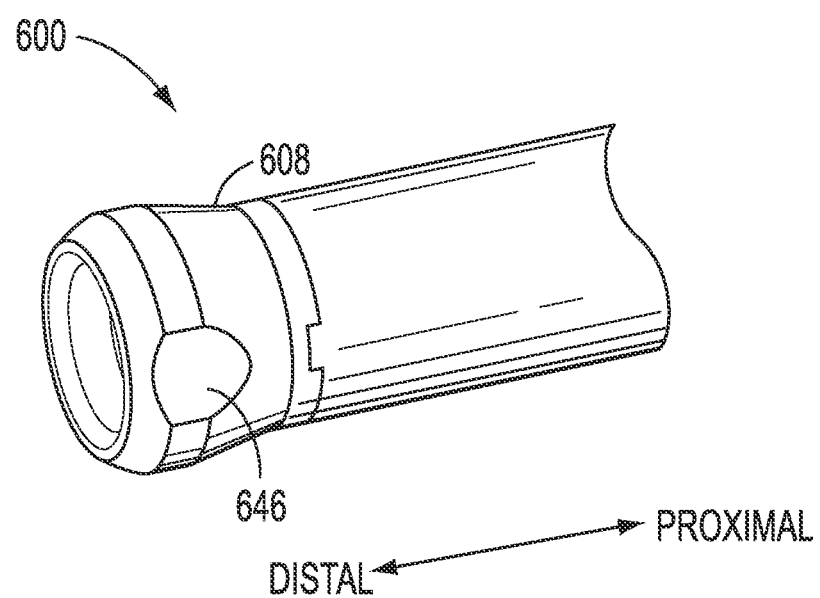
FIG. 6 is a perspective view of a distal end of a reducer device according to an exemplary embodiment of the disclosure.

Referring now to FIG. 6, a perspective view of the distal end of a reducer device 600 is shown. In the exemplary embodiment of FIGS. 6 and 7, an electrically conductive component in the form of a short tube portion 608 extending from the distal end of a main tube portion 602 includes flats 646 and 648 (648 not shown in FIG. 6 due to perspective) formed opposite one another around the outer surface of the electrically conductive tube portion 608. When the reducer device 600 is positioned within the cannula 218, as shown in the distal end view of FIG. 7, the flats 646 and 648 form passages 750 and 752 within the cannula 218 and around the reducer device 600 that facilitate passage of gas and/or liquid through the cannula 218.

Figure 7:
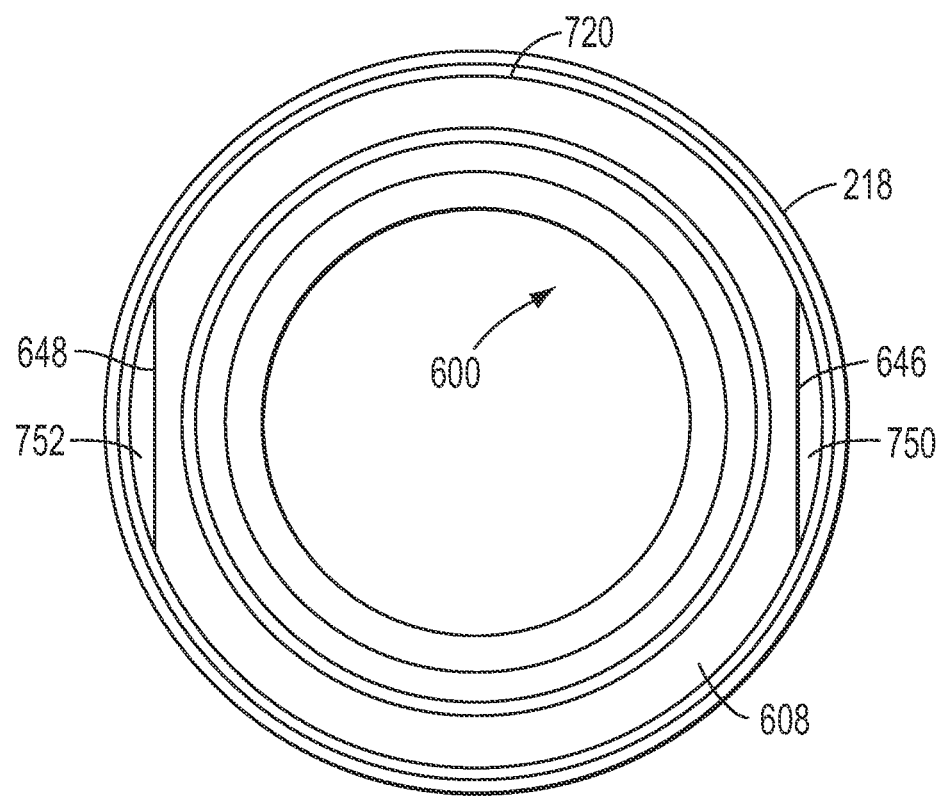
FIG. 7 is a distal end view of the reducer device according to the exemplary embodiment of FIG. 6.

In the embodiment of FIGS. 6 and 7, the flats 646 and 648 are positioned 180 degrees from one another around the circumference of the electrically conductive tube portion 608. The position of a protrusion, such as protrusion 220 discussed above in connection with FIGS. 2 and 3, can be chosen to ensure that the flats 646 and 648 do not compromise the contact or proximity between the electrically conductive tube portion 608 and the cannula 218. For example, as shown in FIG. 7, a protrusion 720 is offset 90 degrees around the circumference of the electrically conductive tube portion 608 from each flat 646 and 648. Locating the protrusion 720 90 degrees from the flats 646 and 648 ensures that the portion of the electrically conductive component 608 biased against the inside wall of the cannula exhibits the full maximum diameter (e.g., the diameter 224 (FIG. 3)) of the electrically conductive tube portion 608 to enhance (e.g., maximize) the contact area between the electrically conductive tube portion 608 and the inside wall of the cannula 218. Stated another way, if either of the flat portions 646 or 648 of the electrically conductive component 608 was biased against the cannula 218, the flat portion 646 or 648 potentially would not form a conductive contact with the cannula 218, because the flat portion would not be in contact with the cannula 218. While two flats 646 and 648 separated by 180 degrees are shown in connection with the exemplary embodiment of FIGS. 6 and 7, other numbers and orientations of flats are contemplated as encompassed by the disclosure, including different shaped reliefs such as channels, bores, or other features that facilitate flow of gas and/or liquid through the cannula and past the electrically conductive tube portion 608 (between the inner wall of the cannula and the electrically conductive tube portion.

In the embodiments described above in connection with FIGS. 1 through 7, the electrically conductive tube portions 108, 208, 608 (FIGS. 1, 2-4, 6, and 7) are positioned at the distal end of the respective reducer devices 100, 200, 600. Such distal end positioning can facilitate creating contact or close proximity between the electrically conductive tube portion and the conductive cannula. For example, because the reducer devices 100, 200, 600 are coupled to the cannula (e.g., cannula 218 in FIG. 2) by the latch (e.g., latches 114, 214) at the proximal end of the reducer device, the distal end of the reducer device is free to deflect into contact with the conductive cannula, as discussed above particularly in connection with FIGS. 2-5. However, other configurations and positions for the latch structures are considered within the scope of the disclosure, such as latches that couple the distal ends or intermediate portions of the reducer device and cannula, or embodiments of reducers and cannulas not including any latches or other connecting structures. Similarly, the positioning of the electrically conductive tube portions at the distal end of the reducer devices is exemplary and not limiting. For example, in other exemplary embodiments, the electrically conductive tube portions are positioned at a proximal location on the reducer device, or positioned on the reducer device at a position intermediate the proximal end and the distal end.

In the exemplary embodiments described above, the electrically conductive tube portion exhibits a length that represents a fraction of the total length (e.g., a distance between the proximal end and the distal end) of the reducer device. For example, and not by way of limitation, the electrically conductive tube portion exhibits a length that is equal to or less than a fraction of the total length of the reducer device, such as one half, one quarter, one tenth, one twentieth, one fiftieth, one hundredth, or any other fraction of the total length of the reducer device without limitation. Accordingly, a conductive path formed between the interior of the reducer device and the exterior and the reducer device can be characterized as being localized along an axial length of the reducer device. As an example, in some exemplary embodiments, the conductive path is localized along an axial length of the reducer device near a distal end of the surgical instrument shaft 419 to ensure that the conductive path is located near the patient's body wall; however, the present disclosure contemplates that the conductive path can be positioned anywhere along the length of the reducer device.

Figure 8:
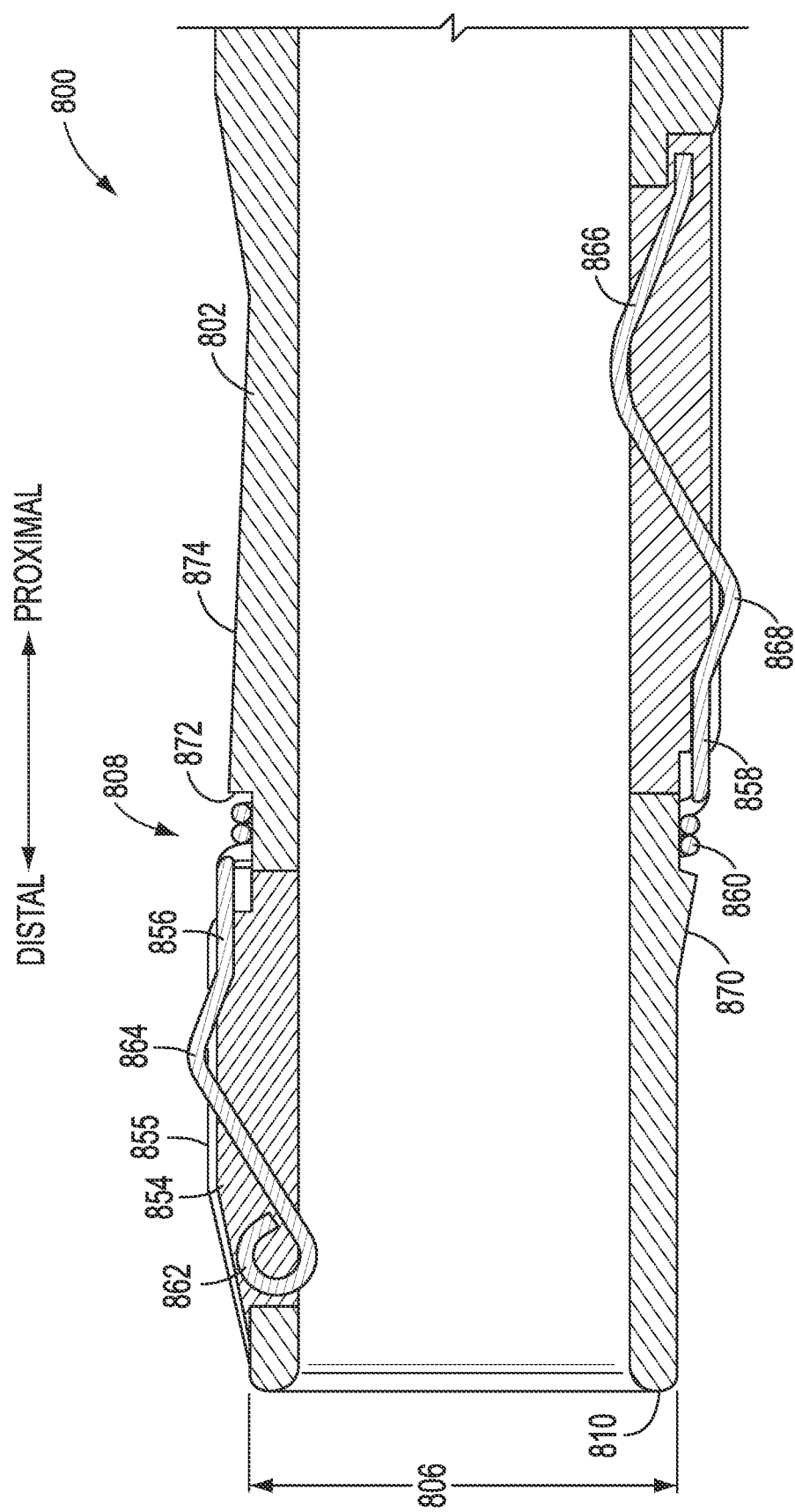
FIG. 8 is a cross-sectional elevation view of a distal end of a reducer device according to another exemplary embodiment of the disclosure.
Figure 9:
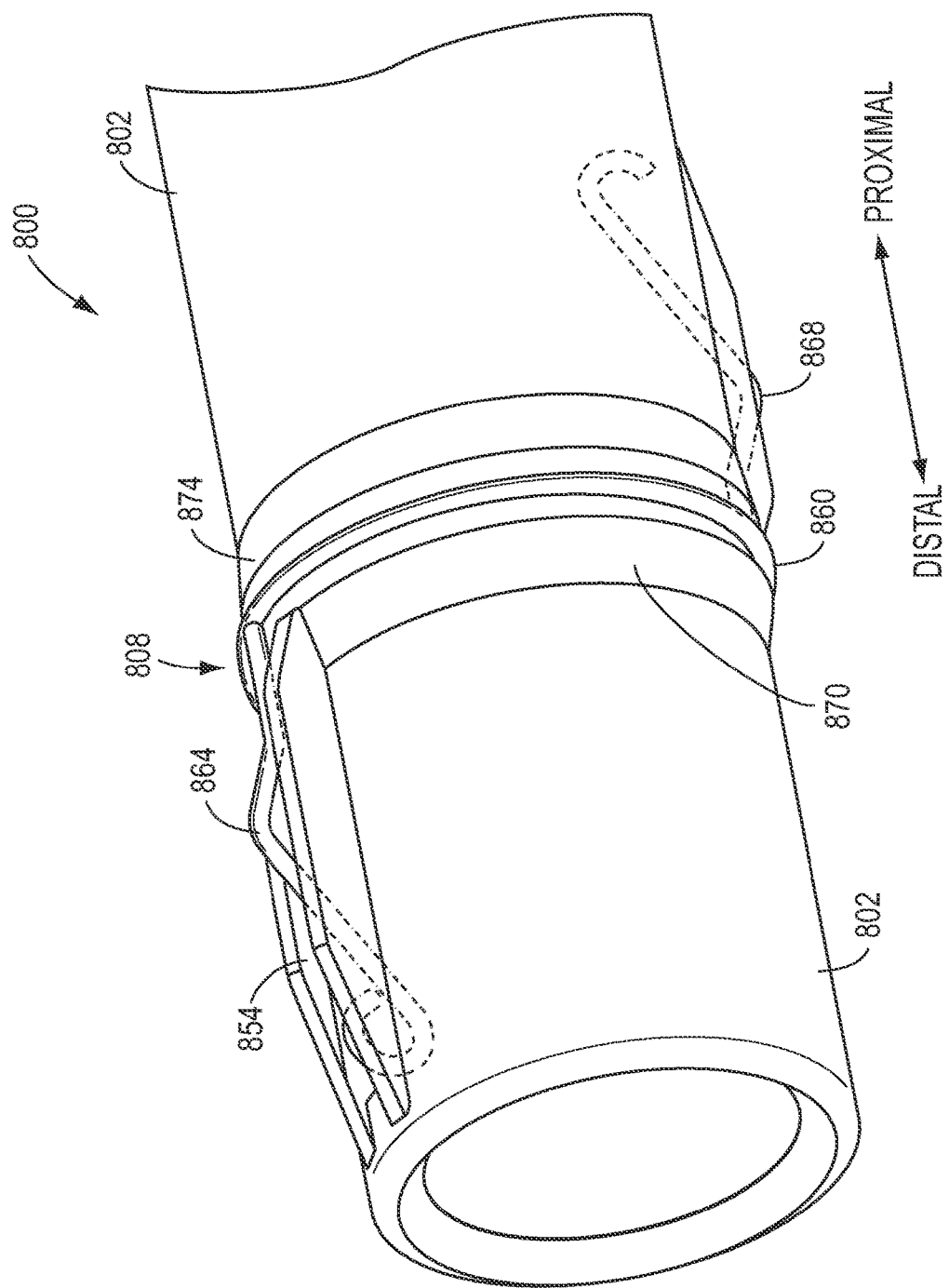
FIG. 9 is a perspective, interior view of the distal end of the reducer device according to the embodiment of FIG. 8.

Other configurations and arrangements of electrically conductive components are encompassed by the present disclosure. For example, yet another exemplary embodiment of a reducer device 800 is shown in FIGS. 8 and 9 which depict the distal end portion of the reducer device 800. Other portions, such as the proximal end, and the portion of the reducer device intermediate the distal and proximal ends, can be similar to those described above in connection with FIGS. 1 through 7. However, the exemplary embodiment disclosed in connection with FIGS. 8 and 9 does not include any protrusion (e.g., protrusion 220 discussed in connection with FIGS. 2 and 5) for reasons discussed below.

In the embodiment of FIGS. 8 and 9, the reducer device 800 includes an elastically deformable electrically conductive component 808 that is configured such that a portion moves resiliently in a radially outward direction relative to the reducer device 800 so as to provide contact or close proximity positioning between the electrically conductive component 808 and a cannula in which the reducer device 800 is positioned. The elastically deformable electrically conductive component 808 has a first arm portion 856 and a second arm portion 858. The first arm portion 856 and second arm portion 858 are connected to one another by a coiled portion 860 wrapped circumferentially around the reducer device 800.

The first arm portion 856 and the second arm portion 858 extend from the coiled portion 860 in generally opposite longitudinal (axial) directions along the reduce device 800, although one of ordinary skill in the art would appreciate that the arms could extend in the same direction as well. The first arm portion 856 includes a free end 862 configured to extend at least partly into an interior of the main tube 802 of the reducer device 800. An elbow 864 of the first arm portion 856 protrudes beyond the outer diameter 806 of the main tube 802 and beyond a wall 855 of the slot 854. Similarly, the second arm portion 858 includes a free end 866 that extends at least partially into the interior of the main tube 802 of the reducer device 800 and an elbow portion 868 that protrudes beyond the outer surfaces of the main tube 802.

As shown in FIGS. 8 and 9, the elastically deformable electrically conductive component 808 is positioned generally toward the distal end of the reducer device 800. However, other placements of the elastically deformable electrically conductive component 808, such as toward the proximal end of the reducer device 800, or various positions intermediate the distal end and proximal end of the reducer device 800, are within the scope of the disclosure. In the exemplary embodiment of FIGS. 8 and 9, the elastically deformable electrically conductive component 808 includes first and second arm portions 856 and 858 oriented in generally opposite directions along a longitudinal axis AL of the reducer device 800 and separated by 180 degrees around the circumference of the reducer device 800. In other exemplary embodiments, arm portions have different arrangements, such as being oriented in the same direction along the longitudinal axis AL, having various orientations not aligned with the longitudinal axis AL, and being separated by angles greater or less than 180 degrees around the circumference of the reducer device 800. Further, other exemplary embodiments include a single arm portion, or three or more arm portions with various arrangements, etc.

In a position in which the reducer device 800 is within a cannula, such as cannula 218 (FIG. 2), the elbow portions 864 and 868 of the respective first and second arm portions 856 and 858 contact the cannula 218. In some exemplary embodiments, the free ends 862 and 866 are deflected inward to some extent by the contact of the elbow portions 864 and 868 against the cannula.

In a position of a surgical instrument shaft (e.g., surgical instrument shaft 419 shown in FIG. 4; not shown in FIG. 8) being inserted into the main tube 802, the free ends 862 and 866 contact the surgical instrument shaft and are deflected outward to some extent by the surgical instrument shaft as the surgical instrument shaft is inserted within the main tube 802, further urging the elbow portions 864 and 868 into contact with the inner wall of the cannula. In this way, constant, consistent conductive contact or proximity between the surgical instrument shaft and cannula through the elastically deformable electrically conductive component 808 can occur. The elastically deformable electrically conductive component 808 thereby forms a conductive path between the surgical instrument shaft and the cannula when the reducer device 800 is positioned in the cannula and the surgical instrument shaft is positioned within the reducer device 800. The exemplary embodiment of the reducer device 800 in FIGS. 8 and 9 does not include any protrusion (e.g., a protrusion such as protrusion 220 discussed in connection with FIGS. 2 and 5), because the elastic nature of the elastically deformable electrically conductive component 808 serves to maintain contact, or proximity sufficient to support electrical conductivity, between the surgical instrument shaft and cannula without the main tube 802 being biased away from a central position within the cannula.

Although the present disclosure contemplates use of a single arm portion for the electrically conductive component, the first and second arm portions 856 and 858 provide redundancy with one another to further impart consistency and reliability to the electrically conductive path between the instrument shaft and cannula. For example, if, under some conditions contact between the first arm portion 856 and either of the cannula and instrument shaft is compromised, contact between the second arm portion 858 is potentially unaffected by the same conditions. Similarly, conditions which could compromise contact and electrical conduction between the second arm portion 858 and the instrument shaft and/or cannula potentially do not affect contact of the first arm portion 856 with the cannula and/or instrument shaft. In this manner, redundancy between the first arm portion 856 and second arm portion 858 provides a reliable and consistent electrically conductive connection between the instrument shaft and cannula.

In other exemplary embodiments, it is contemplated that different numbers of arm portions, such as a single arm portion or more than two arm portions, or different shapes, configurations, and arrangements of arm portions are within the scope of the disclosure. In the embodiment of FIGS. 8 and 9, the elastically deformable electrically conductive component 808 is made from a relatively elastic, electrically conductive material. By way of example and not limitation, such materials as steel alloys such as stainless steels, titanium alloys, or other metallic or non-metallic materials are considered within the scope of the disclosure.

To facilitate assembly of the elastically deformable electrically conductive component 808 with the main tube 802, the main tube 802 includes a ramp portion 870 that extends partially or fully around the circumference of the main tube 802. The elastically deformable electrically conductive component 808 is introduced over the distal end 810 of the main tube 802. The ramp portion 870 causes the coiled portion 860 of the elastically deformable electrically conductive component 808 to deform and expand in diameter to fit over the ramp portion 870. After the coiled portion 860 clears the ramp portion 870, the coiled portion 860 drops behind the ramp portion 870, and the coiled portion 860 returns to its original diameter to retain the elastically deformable electrically conductive component 808 behind the ramp portion 870. In some embodiments, the ramp portion 870, and another ramp portion 874, facilitate insertion and withdrawal of the reducer device 800 within the cannula by preventing the coiled portion 860 from catching on portions of the cannula and/or seal during insertion and withdrawal of the reducer device 800. The ramp portions 870 and 874 define an annular groove 872 extending at least partly around the circumference of the main tube 802 in which the coiled portion 860 of the electrically conductive component is seated.

Figure 10:
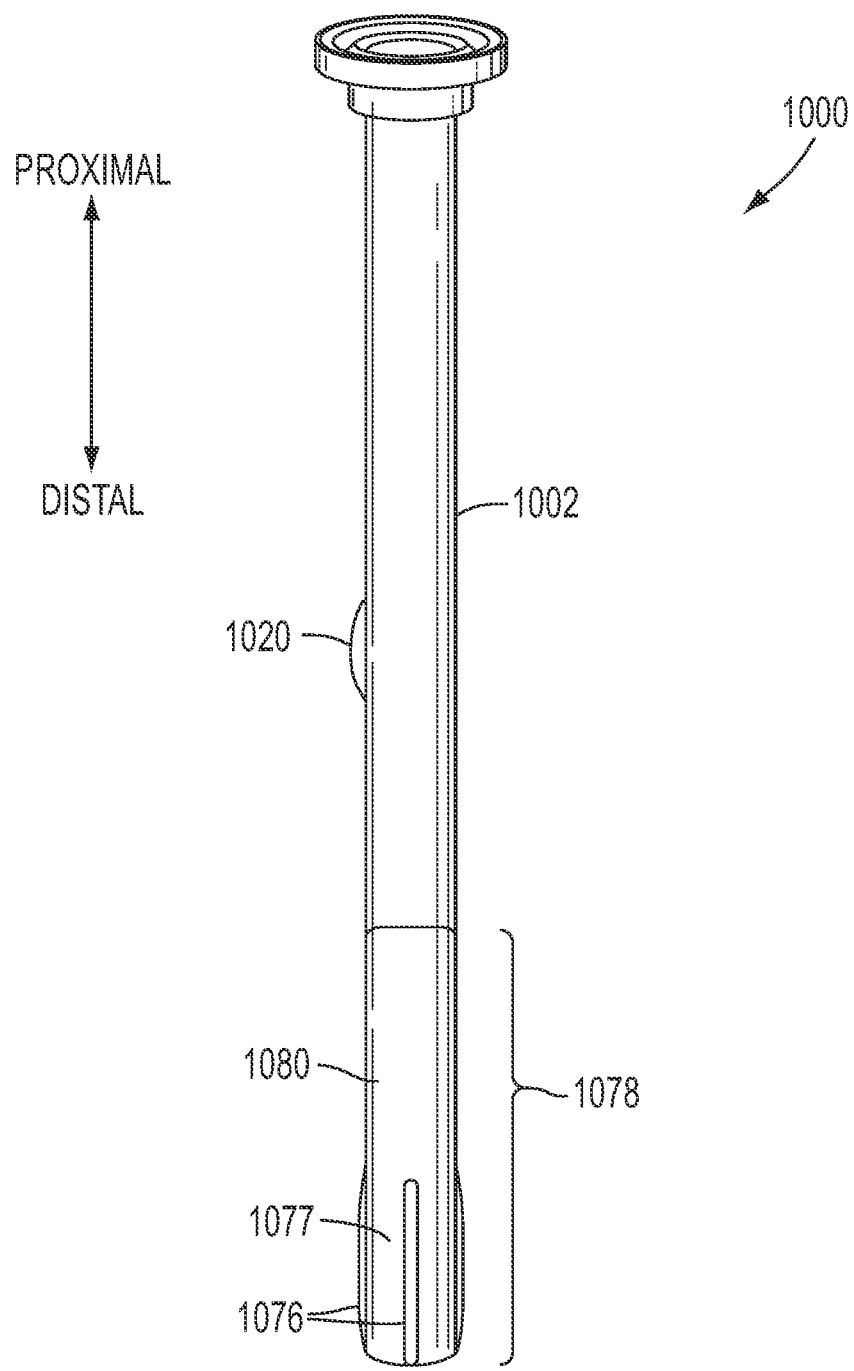
FIG. 10 is a perspective view of a reducer device according to yet another exemplary embodiment of the disclosure.

In some exemplary embodiments, an electrically conductive portion of a reducer device is formed by a coating of electrically conductive material disposed on a portion of a surface of a tube formed of electrically insulating material. For example, referring now to FIG. 10, yet another exemplary embodiment of a reducer device 1000 is shown. In the exemplary embodiment of FIG. 10, the reducer 1000 includes a main tube 1002 made from, e.g., molded polymer, such as the polymer materials discussed above in connection with FIG. 1. The reducer device 1000 includes longitudinal ribs 1076 extending radially from the main tube 1002. In the exemplary embodiment of FIG. 10, the longitudinal ribs 1076 are molded integrally with the main tube 1002. The exterior and interior of a distal portion 1078 of the main tube 1002 are coated with a conductive coating 1080. Such a coating could include a metal or metal alloy deposited by a metallizing process such as, without limitation, electroless plating, vacuum metallizing, thermal spray processes, dip coating, etc. In exemplary embodiments, the metal or metal alloy includes one or more of copper, tin, zinc, aluminum, or other metals. In some exemplary embodiments, the conductive coating 1080 is a conductive paint, e.g., a composite material of electrically conductive metallic or non-metallic particles adhered to the main tube 1002 by an adhesive or other binder material.

Spaces 1077 between the longitudinal ribs 1076 enable passage of insufflation gasses or evacuation of smoke between the reducer 1000 and a cannula (e.g., cannula 218 in FIG. 2) in which the reducer 1000 is positioned. To ensure constant contact between one or more of the longitudinal ribs 1076 and the interior of a cannula in which the reducer 1000 is positioned, the reducer 1000 includes a protrusion 1020 that abuts the interior wall of the cannula to bias the main tube 1002 away from a coaxial position with the cannula and preload the one or more longitudinal ribs 1076 into contact, or proximity sufficiently close to achieve electrical conductivity with resistance levels similar to that exhibited by actual contact, with the cannula 218, similar to the embodiment of FIG. 2 described above. The electrically conductive coating 1080 forms a conductive path between the cannula and a conductive instrument shaft (e.g., instrument shaft 419 shown in FIG. 4) positioned within the main tube 1002 of the reducer 1000. While the embodiment of FIG. 10 includes four longitudinal ribs equally spaced around the circumference of the reducer device 1000 near the distal end of the reducer device 1000, other shapes, numbers, configurations, etc. of ribs or other protrusions, near the distal end, the proximal end, or positions intermediate the distal and proximal end, are encompassed by the present disclosure.

Various exemplary embodiments of the present disclosure provide reducer devices having the capability of conducting electrical current between a surgical instrument shaft and a conductive cannula, thereby enabling constant and controlled dissipation of the electrical current to the patient's body through contact with the cannula. Such reducer devices are configured to maintain contact, or proximity sufficient to support electrical conductivity, between the reducer device and the cannula.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure.

Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms— such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the exemplary embodiments disclosed herein. It is intended that the specification and examples be considered as exemplary only, with the following claims being entitled to their fullest breadth, including equivalents, under the applicable law.

What is claimed is:

1. A reducer device for insertion into a surgical cannula, the reducer device comprising:
   a tubular member comprising a proximal end opening, a distal end opening, and an interior passage having a length extending between the proximal end opening and the distal end opening,
      wherein the interior passage is sized to receive a surgical instrument such that the surgical instrument extends through the length of the interior passage, and
      wherein the tubular member is dimensioned and configured to be inserted within a surgical cannula;
   an electrically conductive component configured and positioned to provide an electrically conductive path from the interior passage of the tubular member to an exterior of the tubular member,
      wherein the electrically conductive path has a height measured in a direction along the length of the tubular member, and
      wherein the height of the electrically conductive path is less than the length of the interior passage; and
   a biasing component positioned to interact with the surgical cannula in the inserted position of the tubular member,
      wherein the biasing component biases the tubular member to a position at which the electrically conductive component contacts the surgical cannula.

2. The reducer device of claim 1, wherein the electrically conductive component is positioned at a distal end portion of the tubular member.

3. The reducer device of claim 1, wherein the electrically conductive component is an electrically conductive tubular portion of the tubular member.

4. The reducer device of claim 3, wherein the electrically conductive tubular portion has an inner diameter, and the tubular member further comprises a main tube portion having an inner diameter larger than the inner diameter of the electrically conductive tubular portion.

5. The reducer device of claim 3, wherein the tubular member further comprises a main tube portion having an external diameter smaller than an external diameter of the electrically conductive tubular portion.

6. The reducer device of claim 1, wherein the electrically conductive component is a portion of the tubular member, and the electrically conductive component comprises an exterior surface and one or more relief features on the exterior surface.

7. The reducer device of claim 6, wherein the one or more relief features comprise one or more flat surfaces.

8. The reducer device of claim 1, wherein the tubular member comprises an exterior surface, and the biasing component comprises a protrusion extending radially from the exterior surface of the tubular member.

9. The reducer device of claim 1, wherein, on a condition in which the reducer device is at an inserted position within a cannula, the biasing component is configured to bias a portion of the tubular member away from coaxial alignment with the cannula.

10. The reducer device of claim 1, wherein the tubular member comprises a proximal end, the reducer comprises a latch mechanism configured to couple the reducer with the surgical cannula, and the latch mechanism is at the proximal end of the tubular member.

11. The reducer device of claim 1, wherein the tubular member comprises a main tube portion made of an electrically insulative material molded with the electrically conductive component.

12. The reducer device of claim 1, wherein the tubular member comprises a polymer material.

13. The reducer device of claim 1, wherein the electrically conductive component comprises a metallic material.

14. The reducer device of claim 1, wherein the biasing component comprises an elastically deformable portion of the electrically conductive component.

15. A surgical assembly, comprising:
a surgical cannula;
a reducer device configured to be inserted within the surgical cannula; and
a surgical instrument configured to be inserted within the reducer device;
wherein the reducer device comprises a tubular member having an exterior surface and a protrusion extending radially from the exterior surface;
wherein the tubular member comprises an electrically insulating material and an electrically conductive structure;
wherein the electrically conductive structure defines an electrically conductive path between the surgical instrument and the surgical; and
wherein on a condition that the reducer device is at an inserted position within the surgical cannula, the protrusion is configured to bias a portion of the tubular member away from coaxial alignment with the surgical cannula.

16. The surgical assembly of claim 15, wherein the surgical instrument is an endoscope.

17. The surgical assembly of claim 15, wherein the electrically conductive structure is an electrically conductive tubular portion of the tubular member.

18. The reducer device of claim 17, wherein the electrically conductive tubular portion has an inner diameter, and the tubular member further comprises a main tube portion having an inner diameter larger than the inner diameter of the electrically conductive tubular portion.

19. The reducer device of claim 17, wherein the tubular member further comprises a main tube portion having an external diameter smaller than an external diameter of the electrically conductive tubular portion.

* * * * *